United States Patent [19]

Sridhar et al.

[11] Patent Number: 4,952,292

[45] Date of Patent: Aug. 28, 1990

[54] PROCESS FOR MANUFACTURING 2,4-HEXADIYNE-1,6-DIOL

[75] Inventors: Srinivasan Sridhar, Marl; Helmut Westernacher, Haltern, both of Fed. Rep. of Germany

[73] Assignee: Huels Aktiengesellschaft, Marl, Fed. Rep. of Germany

[21] Appl. No.: 206,672

[22] Filed: Jun. 15, 1988

[30] Foreign Application Priority Data

Jun. 30, 1987 [DE] Fed. Rep. of Germany ....... 3721474

[51] Int. Cl.$^5$ ............................................. C07C 31/18
[52] U.S. Cl. .................................. 204/180.1; 568/855; 568/856
[58] Field of Search ..................... 204/180.1; 585/505; 568/873

[56] References Cited

U.S. PATENT DOCUMENTS 4,427,507 1/1984 van Aken ........................... 204/151

OTHER PUBLICATIONS

Patel, G. N. "Soluble Polydiacetylenes. I. Synthesis and Properties", Polymer Preparations, American Chemical Society, vol. 19, No. 2, pp. 154–159, (1978).

Primary Examiner—John F. Niebling
Assistant Examiner—Isabelle Rodriquez
Attorney, Agent, or Firm—Oblon, Spivak, McClelland, Maier & Neustadt

[57] ABSTRACT

A method of manufacturing 2,4-hexadiyne-1,6-diol by the oxidative coupling of propargyl alcohol, in the presence of an aliphatic $C_4$ alcohol solvent is disclosed. The 2,4-hexadiyne-1,6-diol is completely dissolved in the butanol. Residual salts dissolved in the butanol solution at the end of the reaction are separated out by electrodialysis. The salt-containing stream which is separated out and contains the catalyst salts, water, and butanol is suitable as a reaction mixture, and can be recycled to the reactor.

16 Claims, 5 Drawing Sheets

PROCESS FOR MANUFACTURING 2,4-HEXADIYNE-1,6-DIOL

BACKGROUND OF THE INVENTION

1. Field of the Invention:

This invention relates to the manufacture of 2,4-hexadiyne-1,6-diol.

2. Disussion of the Background:

2,4-Hexadiyne-1,6-diol may be prepared by hydroxymethylation of diacetylene with formaldehyde. However because of the hazardous nature of diacetylene which has a tendency to decompose explosively, it is recommended that this compound be employed only at high dilution. Consequently, it is difficult to devise an economically feasible process for making 2,4-hexadiyne-1,6-diol by using this approach.

2,4-Hexadiyne-1,6-diol may also be prepared, quite safely, from propargyl alcohol, by oxidative coupling via the Glaser method A suitable process is described in Brandsma, L., 1971, "Preparative acetylenic chemistry", pub. Elsevier, Amsterdam, p. 166.

The disadvantage of this process is that 2,4-hexadiyne-1,6-diol, being relatively insoluble, precipitates out of the reaction mixture and the crystal-containing slurry obtained by this process is costly to refine. In addition, the slurry contains salts of the catalyst for the oxidative coupling of the propargyl alcohol. These salts have to be separated from the product, but because 2,4-hexadiyne-1,6-diol is slightly water-soluble, water washing results in product loss. Separation by distillation is also unsuitable, because 2,4-hexadiyne-1,6-diol is heat-labile; under a vacuum it boils at a higher temperature than water.

The well known ion exchange technique is suitable for recovering the salts from the product if the salt content is not too high. However, when the ion exchanger is regenerated, salt-containing eluates are released, which represent not only loss of product but also an environmental contamination problem.

Use of reverse osmosis for desalination is not an option, because there are problems with the stability of the membranes and with the permeate stream in organic media. And the salt-containing retentate also needs to be further processed.

There is thus a need for a process which permits the economical and safe preparation of 2,4-hexadiyne-1,6-diol, where the salts are removed from the product, where the salts do not cause an environmental problem, and where the 2,4-hexadiyne-1,6-diol product does not crystallize out of the reaction mixture.

SUMMARY OF THE INVENTION

Accordingly, it is an object of this invention to provide a novel process which permits the economical production of 2,4-hexadiyne-1,6-diol.

It is another object of this invention to provide a novel process for the preparation of 2,4-hexadiyne-1,6-diol in which salts associated with the process are removed during the process.

It is another object of this invention to provide a novel process for the preparation of 2,4-hexadiyne-1,6-diol in which the 2,4-hexadiyne-1,6-diol product does not crystallize out of the reaction mixture.

It is another object of this invention to provide a novel process for the preparation of 2,4-hexadiyne-1,6-diol in which the salts removed from the product do not cause an environmental problem.

It is another object of this invention to provide a novel process which permits the safe preparation of 2,4-hexadiyne-1,6-diol.

The inventors have now discovered a process which satisfies all of these objects of this invention, and other objects which will become apparent from the description of the invention given hereinbelow. In this process 2,4-hexadiyne-1,6-diol is obtained by the oxidative catalytic coupling of propargyl alcohol in the presence of a $C_4$ alcohol solvent (butanol).

A reactor is first charged with an oxidative coupling catalyst, propargyl alcohol, butanol, and water to obtain a reaction mixture. This reaction mixture is pressurized with dioxygen to a gauge pressure of from 0.1 to 5 bar, and heated to a temperature of from 5° to 80° C. under vigorous stirring.

When the reaction is complete, the stirring is stopped and a two-phase mixture is obtained This two-phase mixture is separated into a first solution containing 2,4-hexadiyne-1,6-diol in butanol and a second aqueous catalytic solution.

The first solution containing 2,4-hexadiyne-1,6-diol in butanol is subjected to electrodialysis where it is the process stream, and a transfer stream containing propargyl alcohol, butanol and water is used. This electrodialysis produces a first product stream which is a desalinated solution containing 2,4-hexadiyne-1,6-diol, and a second product stream which comprises the catalyst salt, propargyl alcohol, water, and butanol. This second product stream is suitable to be recycled to the reactor as a reaction mixture. The process can be run either continuously, semi-continuously or batchwise.

BRIEF DESCRIPTION OF THE FIGURES

A more complete appreciation of this invention and many of its attendant advantages will be readily obtained as the same becomes better understood by reference to the following detailed description when considered in connection with the accompanying figures, wherein.

DETAILED DESCRIPTION OF THE PREFERRED EMBODIMENTS

The inventors have now surprisingly discovered that one can avoid precipitation of the 2,4-hexadiyne-1,6-diol which is being produced if butanol is added to the reaction mixture. A two-phase heterogeneous mixture forms wherein the 2,4-hexadiyne-1,6-diol is practically completely dissolved in the butanol. After the reaction is completed and the stirrer is turned off, the butanol solution containing the 2,4-hexadiyne-1,6-diol quickly and distinctly separates out from the aqueous catalyst solution, by phase separation.

Suitable butanols are n-, iso-, and tert-butanol. The ratio of catalyst phase to butanol phase is in the range 5:1 to 1:5 (v/v), preferably 3:1 to 1:2, particularly preferably 2:1. Preferably, a 5 to 50% (v/v), particularly a 10 to 30%, solution of propargyl alcohol in the butanol and possibly water (stream 2 in FIG. 1) is introduced into the aqueous catalyst solution, under stirring.

Generally, copper salt complexes in aqueous solution are used as catalyst, e.g., a cuprous chloride/ammonium chloride complex.

Figure 1:
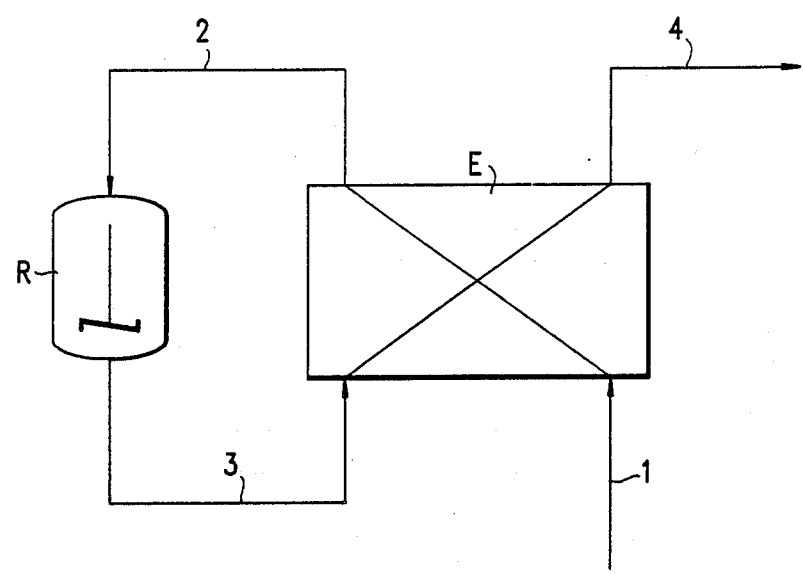
FIG. 1 illustrates a reactor/electrodialysis system which can be used to run the process of the present invention.
Figure 2:
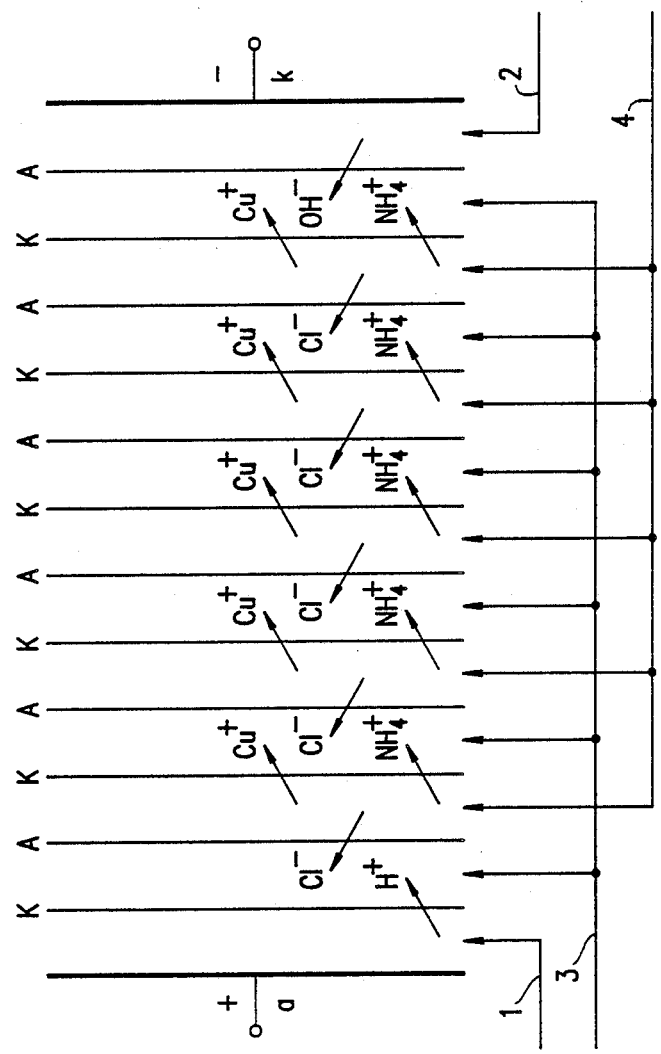
FIG. 2 illustrates the structure of the dialysis array used in Example 1.
Figure 3:
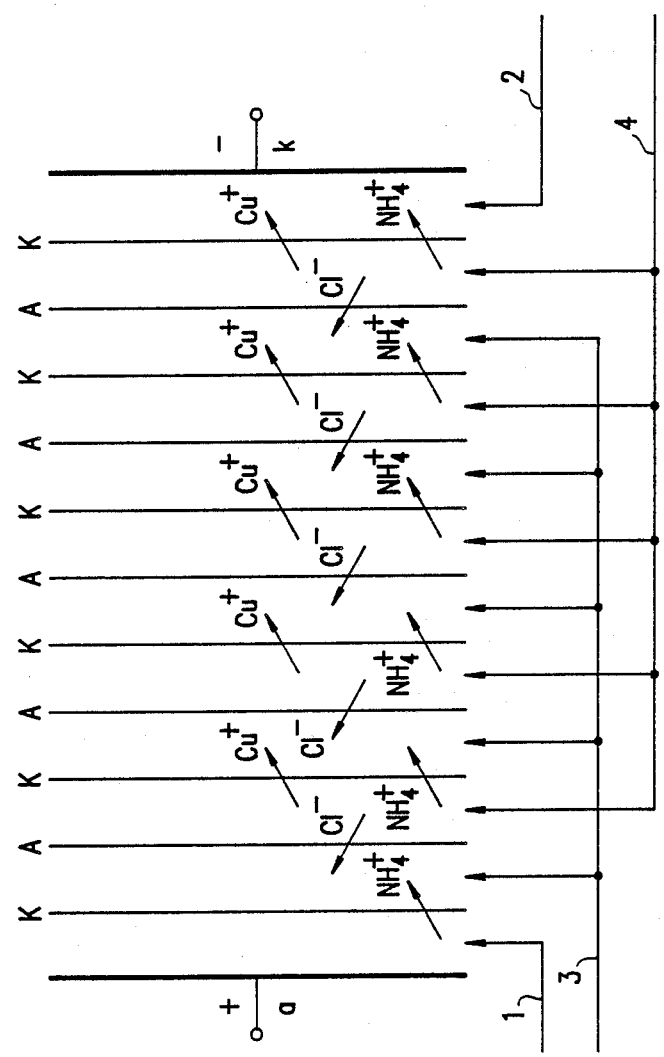
FIG. 3 illustrates the structure of the dialysis array used in Example 2.

The reaction is carried out, in general, in a pressure reactor equipped with a stirrer, pressure maintenance valve, and thermometer (reactor R in FIG. 1). The aqueous catalyst solution is charged into the reactor. The catalyst solution is prepared to comprise, e.g., cuprous chloride 2 to 8 wt.%, ammonium chloride c. 10 to 26 wt.%, and water c. 66 to 88 wt.%. Catalyst solutions with lower salt concentrations are undesirable because they result in uneconomically long reaction times and they may lose the capability of catalyzing the oxidative coupling.

The reaction mixture is brought to the reaction temperature, namely 5° to 80° C., preferably 10° to 50° C., and the Glaser coupling reaction is initiated by pressurizing with oxygen. The reaction heat generated by the reaction is removed by a cooling means. During the reaction the pressure is maintained at 0.1 to 5 bar gauge, preferably 0.5 to 3 bar gauge. Air may be used in lieu of pure oxygen, in which case a continous gas bleed from the reactor must be provided for in order to maintain the necessary oxygen concentration. The reaction is concluded when the propargyl alcohol content falls below 0.5% (v/v). The method may be carried out in a continuous or batchwise mode.

The reactor is depressurized, the stirrer is turned off, and the butanol phase which separates out (top layer) is removed. The catalyst solution remains in the reactor, and may be used for additional reactions.

The butanol phase still contains residual amounts of salts (c. 0.1 to 2 wt.%). According to the invention, the residual amounts of salts are removed by electrodialysis. The transfer solution (also called "receiving solution") comprises butanol, which is an organic solvent inherent to the system (which solvent does not contain the product and contains a small amount of water), and propargyl alcohol. As a result of the electrodialysis the salts are separated out of the reaction mixture and may be recycled with the transfer solution to catalyze the reaction. Thus, the desalination and salt recovery entail no environmental contamination.

The reaction mixture leaves the reactor R as stream 3 (FIG. 1), which is fed to the electrodialyzer E wherein the salts are removed, e.g., in a membrane array E. The membranes employed may be known commercially available types. Preferably the chamber width is 0.3 to 3 mm and the membrane thickness is 0.1 to 0.3 mm.

In general the membranes are comprised of styrene-divinylbenzene with (chemically) added functional groups, on a fabric comprised of polyvinyl chloride (for cation exchange membranes "K") or polypropylene (for anion exchange membranes "A"). The cation- or anion-exchange activity is brought about by, e.g., added sulfonate or quaternary ammonium groups.

In general a voltage of 2 to 10 V is applied to each pair of chambers. The specific conductivity of the starting mixture is generally 400 to 1000 $\mu$mho/cm, and the current density is 0.1 to 50 mA/sq cm. During the electrodialysis the specific conductivity decreases, and consequently the current also decreases. The electrodialysis is generally carried out at low temperature, preferably 10° to 40° C., particularly preferably 20° to 30° C.

The electrode array is comprised of alternating "A" and "K" membranes, disposed between two electrodes. The electrodes themselves may have acid, alkali, or salt solutions, respectively, flowing over them. A chamber is formed by two membranes. Two neighboring chambers, bearing the transfer solution and process solution (also called "supply solution"), respectively, together form a functioning cell. The array comprises two groups of membrane chambers (which are to be connected in parallel), which groups bear, respectively, the transfer and process solutions (see the Examples). If the streams are passed in recirculation loops, continuous desalination takes place. However, if a sufficient processing path is provided (with sufficient membrane chambers and arrays), the desalination can be accomplished in a single pass.

A mixture of propargyl alcohol, butanol, and water is suitable as stream 1 (the transfer stream) in the electrodialysis array E. This stream becomes rich in cuprous chloride and ammonium chloride The salt-containing stream 2 corresponds to the desired reaction mixture, and is fed to the reactor R where the reaction to form 2,4-hexadiyne-1,6-diol takes place. The reaction mixture is then passed (as stream 3, the process stream) to the electrodialysis array, where desalination is carried out. Streams 2 and 3 form a salt recycle loop.

The 2,4-hexadiyne-1,6-diol from the electrodialysis (stream 4 in FIG. 1) is then sent to refining or further processing. An example of possible further processing is hydrogenation to 1,6-hexanediol. In a downstream column, 1,6-hexanediol and butanol can be separated. The butanol recovered is used in the transfer stream of the electrodialysis and then is sent as stream 1 via the electrodialysis to the reactor for converting the propargyl alcohol. The electrodialytic desalination may be carried out continuously, semicontinuously, or batchwise. Preferably the operation is continuous; however, in special cases a batchwise operation may be advantageous.

Other features of the invention will become apparent in the course of the following descriptions of exemplary embodiments which are given for illustration of the invention and are not intended to be limiting thereof.

EXAMPLES

Example 1.1

A solution of 92.5 g cuprous chloride and 300 g ammonium chloride in 1000 g water was introduced into a 2-liter autoclave. A solution of 140.3 g propargyl alcohol in 500 g butanol was added to this catalyst mixture. The reaction mixture was heated to 30° C. under stirring (700 rpm), and was purged of nitrogen by passing oxygen through it. Then a reaction pressure $P_e$ of 0.5 bar gauge was established. The heat of reaction was removed by water cooling. After 100 min the reaction was terminated. (Propargyl alcohol content <0.1.)

The reactor was depressurized, the stirrer was turned off, and the butanol phase (700 g) was drawn off by suction. The conversion of propargyl alcohol to 2,4-hexadiyne-1,6-diol was nearly quantitative.

The butanol phase was sent to electrodialysis for desalination.

Example 1.2 (FIGS. 1–4, Tables 1–3)

The electrodialysis array contained alternating "K" and "A" membranes, wherewith a K was nearest the anode (a), and an A was nearest the cathode (k). The anode was bathed with 1 wt.% sulfuric acid (stream 1, FIG. 2), and the cathode was bathed with 0.5 wt.% sodium hydroxide (stream 2, FIG. 2). The array contained 6 membrane chambers for the transfer solution (3) and 5 chambers for the process solution (reaction mixture) (4). A cell Q was used to monitor the conductivity of the reaction mixture over the course of the operation (see FIG. 4). The compositions of the solutions and the other technical data are summarized in Tables 1 and 3. After 5 hr 45 min, 93% of the salts (on a chlorine basis) were transferred, with a mean current efficiency of 80%. After an additional 4 hr 50 min, desalination had reached 97% (Table 2).

TABLE 1

| Test Setup | | | |
|---|---|---|---|
| Membrane array: | Overall cell walls comprised of hard PVC in example 1.2 and 2.2. No cell walls in example 3. "K" membranes comprised of styrene-divinylbenzene with sulfonate groups attached. "A" membranes comprised of styrene-divinylbenzene with amino groups attached. | | |
| | Chamber width: | | 3 mm |
| | Membrane thickness: | | 0.2 mm |
| | Effective surface per membrane: | | 100 cm$^2$ |
| Example | | 1.2 | 2.2 |
| Number of Membranes | | | |
| (Cation exchanger) | | 5 | 7 |
| (Anion exchanger) | | 5 | 6 |
| Total effective membrane surface (m$^2$) | | 0.10 | 0.12 |
| Anolyte composition: | | 1% H$_2$SO$_4$ | 1% NH$_4$Cl |
| Catholyte composition: | | 0.5% NaOH | 1% NH$_4$Cl |

| | Example 3 | |
|---|---|---|
| Membran array: | Overall cell walls comprised of Ion exchange membranes as in previous examples | |
| | Chamber width: | 0.4 mm |
| | Membrane thickness: | 0.2 mm |
| | Effective membrane area: | 220 cm$^2$ |
| Number of Membranes | (Cation exchanger) | 25 |
| | (Anion exchanger) | 26 |
| Total effective membrane surface (m$^2$) | | 0,55 |
| Anolyte and catholyte composition: | | 1% NH$_4$Cl |

TABLE 2

Data from Example 1.2

| Salt content of starting mixture: | 212.5 miliequivalents (mval) (see Table 3 for concentrations). |
|---|---|
| Volumetric rate of flow in the circulation loops: | 230 liter/hr. |
| Volumetric rate of flow in the electrolyte baths: | 70 and 115 liter/hr |
| Temperature in all recycle loops: | 30° C. |
| Pressure upstream of the membrane array: | 1.3 bar. |
| Voltage across the entire array, during entire experiment: | 44.5 V |

| Duration (min) | Specific conductivity of the starting mixture (μmho/cm) | Current, I (mA) | Conversion up to the time indicated | |
|---|---|---|---|---|
| | | | (mval) | (%) |
| 0 | 600 | — | | |
| 30 | 455 | 312 | | |
| 51 | 433 | 316 | | |
| 75 | 385 | 318 | | |
| 90 | 332 | 307 | | |
| 160 | 222 | 259 | | |
| 218 | 138 | 197 | | |
| 265 | 97 | 158 | | |
| 305 | 70.8 | 128 | | |
| 345 | 53.3 | 108.6 | 198.5 | 93.4 |
| 380 | 42.2 | 93.5 | | |
| 395 | 28.2 | 75.3 | | |
| 455 | 24.0 | 70.2 | | |
| 550 | 21.4 | 65.7 | | |
| 600 | 20.9 | 64.0 | | |
| 635 | 20.7 | 64.9 | 205.9 | 96.9 |

TABLE 3

| Analytical Results for Example 1.2 | | | | |
|---|---|---|---|---|
| Reaction Mixture: | 20 wt. % 2,4-hexadiyne-1,6-diol, 70 wt. % butanol, and 10 wt. % water. | | | |
| Transfer solution: | 70 wt. % butanol, 20 wt. % propargyl alcohol, and 10 wt. % water. | | | |

| | Duration of experiment (min) | Concentration (ppm by wt.) | | |
|---|---|---|---|---|
| | | NH$_4$$^+$ | Cu | Cl |
| Reaction mixture: | 0 | 1,300 | 400 | 2,600 |
| | 345 | 85 | 65 | 171 |
| | 635 | 60 | 40 | 82 |
| Transfer solution: | 0 | 1,680* | 0 | 3,320 |
| | 345 | 1,700 | 110 | 4,600 |
| | 635 | 2,000 | 140 | 4,900 |

The values for NH$_4$$^+$ are rough approximations.
*Transfer solution initially contains NH$_4$Cl in the amount of 0.5% to provide conductivity.

Example 2.1

The procedure was as in Example 1.1, but air was used instead of pure oxygen, as the oxygen source. Consequently, there was a continous gas bleed of 20 liter/hr. Reaction time was 685 min. The conversion was nearly quantitative.

Example 2.2

Means were employed to prevent the passage of H$^+$ ions out of the anolyte chamber and OH$^-$ ions out of the catholyte chamber in furtherance of electrolysis of water. A 1 wt.% ammonium chloride solution was used in both electrode recycle loops (1 and 2). Only a shifting of the ammonium, Cu$^+$, and chloride ions occurred. (The loss of Cu$^+$ ions into the catholyte can be minimized by having a large number of cells between the electrodes.) The array was comprised of 5 transfer-solution chambers and 5 starting-mixture chambers. After 6 hr 50 min, 75% of the salts (on the basis of the chlorine) were transferred, with a mean yield of 62%. After an additional 15 hr 46 min, the desalination reached 96% (Table 4).

TABLE 4

Data from Example 2.2

| Salt content of starting mixture: | 345 miliequivalents (mval) (see Table 5 for concentrations). |
|---|---|
| Volumetric rate of flow in the circulation loops: | 230 liter/hr. |
| Volumetric rate of flow in the electrolyte baths: | 80 and 150 liter/hr |
| Temperature in all recycle loops: | 30° C. |
| Pressure upstream of the membrane array: | 1.3 bar. |
| Voltage across the entire array, during entire experiment: | 45 V |

| Duration (min) | Specific conductivity of the starting mixture (μmho/cm) | Current, I (mA) | Conversion up to the time indicated | |
|---|---|---|---|---|
| | | | (mval) | (%) |
| 0 | 473 | 277.5 | | |

TABLE 4-continued

| | | |  |  |
|---|---|---|---|---|
| 6 | 466 | 287 | 6 | |
| 36 | 447 | 294.5 | | |
| 90 | 417 | 292.5 | | |
| 120 | 388 | 284.0 | | |
| 150 | 355 | 288.6 | | |
| 230 | 292 | 283.6 | | |
| 280 | 243 | 264.2 | | |
| 340 | 199 | 237.8 | | |
| 400 | 165.1 | 210 | | |
| 410 | | | 266.6 | 75.1 |
| 442 | 137.7 | 191.3 | | |
| 540 | 95.1 | 144.6 | | |
| 750 | 44.7 | 85.5 | | |
| 990 | data lacking | 62.7 | | |
| 1110 | data lacking | 56.1 | | |
| 1230 | data lacking | 55.4 | | |
| 1356 | 25.0 | 52.5 | 341.4 | 96.2 |
| 1410 | 26.6 | 53.5 | | |
| 1470 | 26.9 | 54.1 | | |
| 1530 | 27.2 | 54.1 | | |
| 1590 | 27.2 | 53.6 | 343.7 | 96.8 |

TABLE 5

Analytical Results for Example 2.2

Reaction Mixture: 20 wt. % 2,4-hexadiyne-1,6-diol, 70 wt. % butanol, and 10 wt. % water.

Transfer solution: 70 wt. % butanol, 20 wt. % propargyl alcohol, and 10 wt. % water.

| | Duration of experiment (min) | Concentration (ppm by wt.) | | | |
|---|---|---|---|---|---|
| | | NH$_4^+$ | Cu (a) | (b) | Cl |
| Starting mixture | 0 | 1180 | 280 | 340 | 2350 |
| Begin 5337 g | 410 | 990 | 120 | 140 | 585 |
| End 4895 g | 1356 | 60 | 45 | 40 | 90 |
| | 1590 | 20 | 30 | 40 | 75 |
| Transfer circulation loop | 0 | 1180 | 5 | 6 | 2870 |
| Begin 4996 g | 410 | 1690 | 40 | 130 | 4400 |
| End 5394 g | 1356 | 1590 | 150 | 210 | 4540 |
| | 1590 | 1580 | 160 | 200 | 4430 |

Example 3 (FIG. 1, 4, 5, Tables 6, 7)

The starting mixture was prepared as in example 2.

Figure 4:
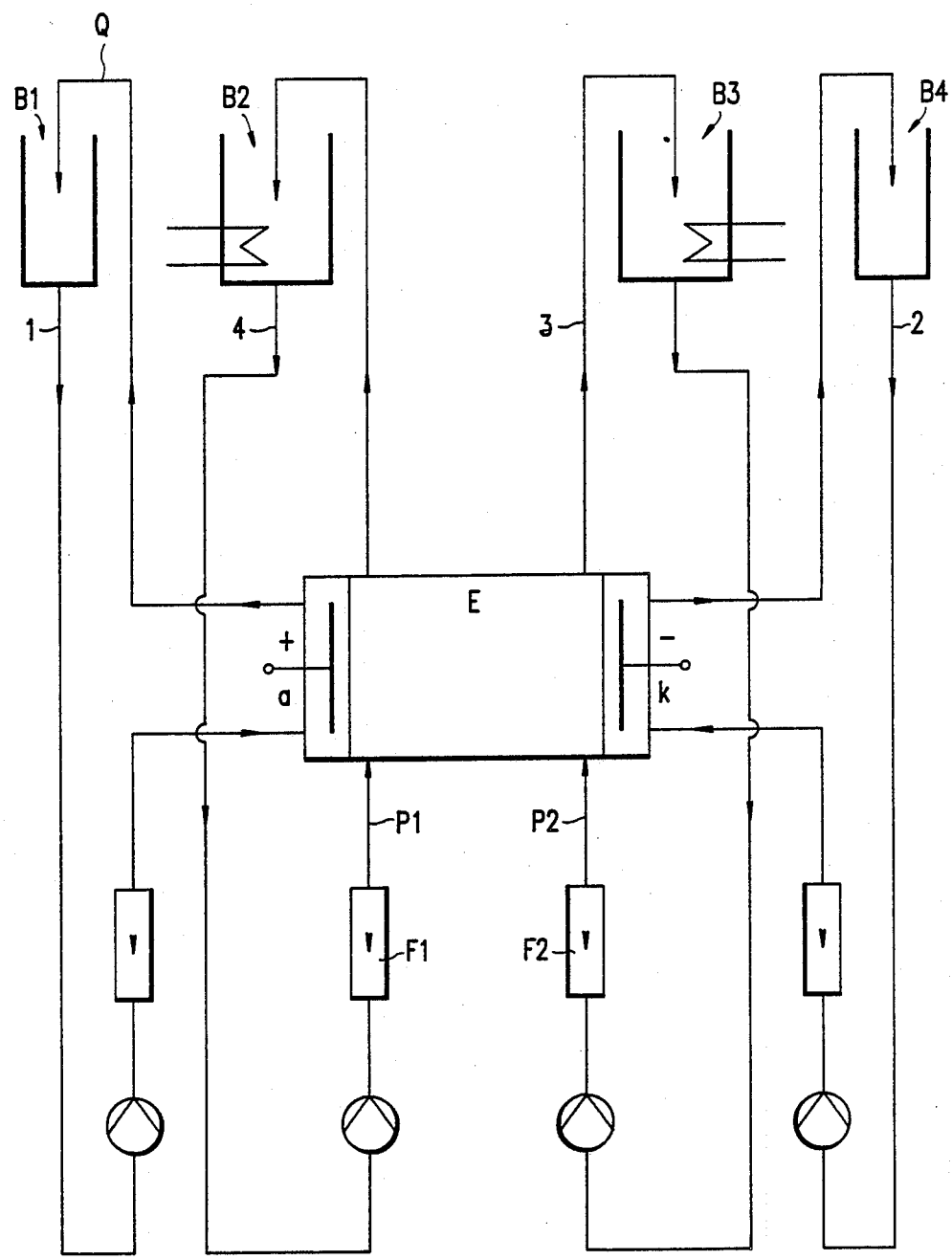
FIG. 4 illustrates the structure of the dialysis array used in Example 3.
Figure 5:
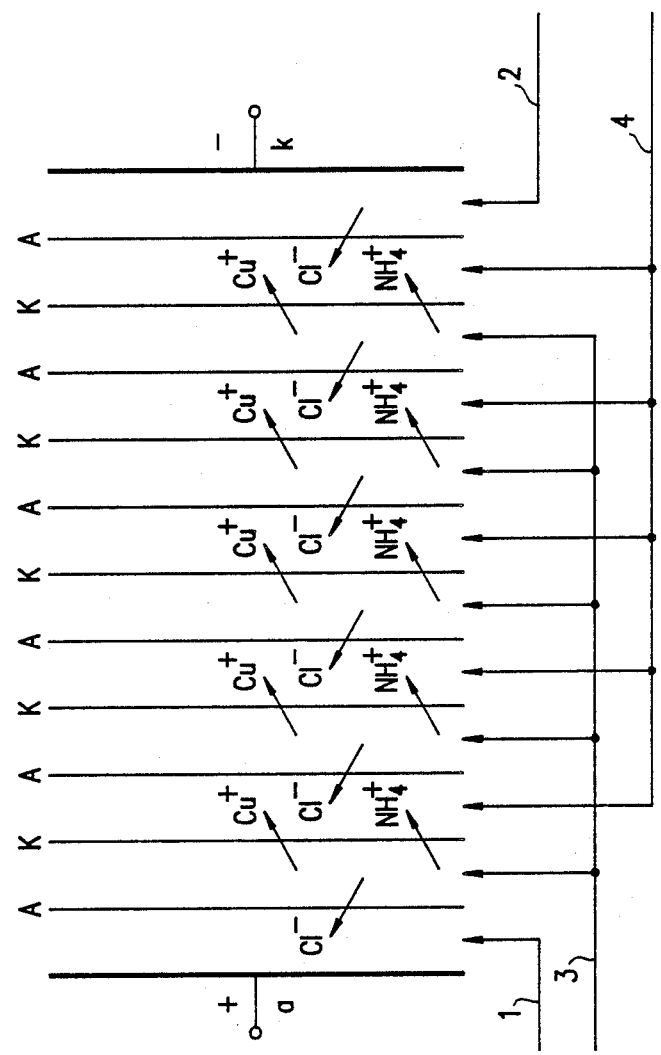
FIG. 5 illustrates an experimental system which can be used with the present invention.

In order to cope with the low conductivity a different electrodialysis stack with a cell width of 0.4 mm and membrane area 220 cm² was employed. Also the dialysis arrag was so chosen that Cu⁺-ions can be contained within the two cycles (FIG. 4). The electrolyte baths have a common source bath being circulated through the same reservoir. Initially only half the available transfer solution, viz., 4136 g was employed. After about 200 minutes the system was cleaned and the diluate (8403g) further desalted with the remaining fresh transfer solution (4136g). A very low salt concentration in the diluate could be realised in a shorter duration.

TABLE 6

Data from Example 3

| | |
|---|---|
| Salt content of starting mixture: | 2260 miliequivalents (mval) (see Table 7 for concentrations). |
| Volumetric rate of flow in the circulation loops: | 280 liter/hr. |
| Volumetric rate of flow in the electrolyte baths: | 530 liter/hr |
| Temperature in all recycle loops: | 25° C. |
| Pressure upstream of the membrane array: | 1,25 bar |
| Voltage across the entire array, during entire experiment: | 75 V |

TABLE 6-continued

| Duration (min) | Specific conductivity of the starting mixture (μmho/cm) | Current, I (mA) | Conversion up to the time indicated | |
|---|---|---|---|---|
| | | | (mval) | (%) |
| 0 | 1110 | — | | |
| 9 | 1082 | 1974 | | |
| 12 | 1045 | 1679 | | |
| 22 | 858 | 1460 | | |
| 42 | 326 | 1260 | | |
| 57 | 143 | 566 | | |
| 77 | 49 | 260 | | |
| 112 | 20,1 | 134 | | |
| 132 | 18,4 | 119 | | |
| 197 | 14,5 | 98 | 73 | 96,8 |
| 203 | 17,4 | 90 | | |
| 209 | 15,6 | 81 | | |
| 213 | 13,3 | 73 | | |
| 219 | 10,0 | 68 | | |
| 234 | 7,3 | 58 | | |
| 257 | 4,8 | 50 | | |
| 282 | 3,9 | 45 | | |
| 312 | 3,3 | 43 | 61 | 97,3 |
| 342 | 3,0 | 42 | | |

TABLE 7

Analytical Results for Example 3

Reaction Mixture: 1,4 wt. % propargyl alcohol, 9,2 wt. % 2,4-hexadiyne-1,6-diol, 75,4 wt. % butanol, and 14 wt. % water.

Transfer solution: 71 wt. % butanol, 15 wt. % propargyl alcohol, and 14 wt. % water.

| | Duration of experiment (min) | Concentration (ppm by wt.) | | |
|---|---|---|---|---|
| | | NH$_4^+$ | Cu | Cl |
| Reaction mixture: | 0 | 1,900 | 2600 | 5500 |
| | 197 | 90 | 130 | 58 |
| | 342 | 90 | 100 | 24 |
| Transfer solution: | 0 | 50 | 0 | 64 |
| | 197 | 2900 | 3200 | 9400 |
| (Fresh solution after 197 Min.) | 342 | ≦50 | 60 | 405 |

The values for NH$_4^+$ are rough approximations.

Obviously, numerous modifications and variations of the present invention are possible in light of the above teachings. It is therefore to be understood that within the scope of the appended claims, the invention may be practiced otherwise than as specifically described herein.

WHAT IS CLAIMED AS NEW AND DESIRED TO BE SECURED BY LETTERS PATENT OF THE UNITED STATES IS:

1. A process for manufacturing 2,4-hexadiyne-1,6-diol by the oxidative catalytic coupling of propargyl alcohol, comprising:

(1) charging a reactor with an oxidative coupling catalyst, propargyl alcohol, butanol and water to obtain a reaction mixture;

(2) pressurizing said reaction mixture with oxygen to a gauge pressure of from 0.1 to 5 bar and heating said reaction mixture to a temperature of 5° to 80° C. with concomittent vigorous stirring;

(3) obtaining a two-phase mixture at the end of the reaction by ceasing said stirring;

(4) separating said two-phase mixture into a first solution of 2,4-hexadiyne-1,6-diol in butanol and a second aqueous solution;

(5) subjecting said first solution of 2,4-hexadiyne-1,6-diol in butanol to electrodialysis as the process stream therein, using as the transfer stream in said electrodialysis a solution comprising propargyl alcohol, butanol, and water;

(6) obtaining as the first product stream from said electrodialysis a desalinated solution comprising 2,4-hexadiyne-1,6-diol and as a second product stream a solution comprising catalyst salt, propargyl alcohol, water and butanol.

2. The process of claim 1, wherein said second product stream comprising the catalyst salt, propargyl alcohol, water and butanol is recycled to said reactor.

3. The process of claim 2, comprising running said process continuously.

4. The process of claim 2, comprising running said process semi-continuously.

5. The process of claim 1, comprising running said process in a batchwise manner.

6. The process of claim 1, wherein said butanol is n-butanol, iso-butanol or tert-butanol.

7. The process of claim 1, wherein said catalyst and said butanol are used in an amount such that the ratio of catalyst to butanol phase is 5:1 to 1:5.

8. The process of claim 7, wherein said ratio is 3:1 to 1:2.

9. The process of claim 1, wherein said catalyst comprises a cuprous chloride/ammonium chloride complex 10. The method of claim 1, wherein said electrodialysis is carried out from a temperature of 10° to 40° C.

11. The process of claim 1, wherein said electrodialysis is carried out at a temperature of from 20° to 30° C.

12. The process of claim 1, comprising charging said reactor in step (1) with a 5 to 50% (v/v) solution of propargyl alcohol and butanol.

13. The process of claim 1, wherein said reactor is charged in step (1) with a catalyst solution comprising 2 to 8 wt.% cuprous chloride, 10 to 26 wt.% of ammonium chloride and 66 to 88 wt.% of water.

14. The process of claim 1, comprising using a temperature from 10° to 50° C. in step (2).

15. The process of claim 1, comprising using an oxygen gauge pressure of from 0.5 to 3 bar.

16. The process of claim 1, comprising ceasing said vigorous stirring of step (2) when the propargyl alcohol content of said reaction mixture in step (2) falls below 0.5% (v/v).

* * * * *